US 6,641,594 B2

(12) United States Patent
Aufaure et al.

(10) Patent No.: US 6,641,594 B2
(45) Date of Patent: Nov. 4, 2003

(54) DEVICE FOR SURGERY OF THE CORNEA

(75) Inventors: Jean-Luc Aufaure, Souvigny (FR); Antoine Sempe, Issy les Moulineaux (FR)

(73) Assignee: Moria SA, Antony (FR)

( * ) Notice: Subject to any disclaimer, the term of this patent is extended or adjusted under 35 U.S.C. 154(b) by 0 days.

(21) Appl. No.: 09/974,816

(22) Filed: Oct. 12, 2001

(65) Prior Publication Data

US 2002/0045910 A1 Apr. 18, 2002

(30) Foreign Application Priority Data

Oct. 12, 2000 (FR) .......................................... 00 13067

(51) Int. Cl.$^7$ .................................................. A61F 9/00
(52) U.S. Cl. ...................................................... 606/166
(58) Field of Search ................................. 606/166, 167, 606/169, 172, 180, 178

(56) References Cited

U.S. PATENT DOCUMENTS

| | | | |
|---|---|---|---|
| 4,423,728 A | | 1/1984 | Lieberman |
| 4,662,370 A | * | 5/1987 | Hoffmann et al. .......... 606/166 |
| 5,586,980 A | | 12/1996 | Kremer et al. |
| RE35,421 E | | 1/1997 | Ruiz et al. |
| 5,624,456 A | | 4/1997 | Hellenkamp |
| 5,944,731 A | * | 8/1999 | Hanna ......................... 606/166 |
| 5,980,543 A | | 11/1999 | Carriazo et al. |
| 6,165,189 A | * | 12/2000 | Ziemer ........................ 606/166 |
| 6,183,488 B1 | * | 2/2001 | Ross et al. ................... 606/166 |
| 6,228,099 B1 | * | 5/2001 | Dybbs ......................... 606/166 |
| 6,358,260 B1 | * | 3/2002 | Ross et al. ................... 606/166 |
| 6,527,788 B1 | * | 3/2003 | Hellenkamp ................. 606/166 |
| 6,551,336 B2 | * | 4/2003 | Sugimura .................... 606/166 |

FOREIGN PATENT DOCUMENTS

| | | |
|---|---|---|
| EP | A2 1 027 873 | 8/2000 |
| WO | WO 95/31143 | 11/1995 |
| WO | A1 99/26568 | 6/1999 |

* cited by examiner

Primary Examiner—Michael J. Milano
Assistant Examiner—Victor X Nguyen
(74) Attorney, Agent, or Firm—Birch, Stewart, Kolasch & Birch, LLP

(57) ABSTRACT

A device for surgery of the cornea includes an annular base for fixing the apparatus to the eye of a patient. A cutter head includes a body and a blade. The cutter head is displaced along a plane trajectory, parallel to the base. A guide is provided on the base and guides the cutter head relative to the base. A first drive imparts movement to the blade in the cutter head with a reciprocating linear motion parallel to the blade's cutting edge. A second drive imparts movement to the cutter head relative to the base along the trajectory. The first and second drives include independent motor units surmounting the cutter head and having mutually parallel outlet shafts perpendicular to the plane of the trajectory of the cutter head.

20 Claims, 7 Drawing Sheets

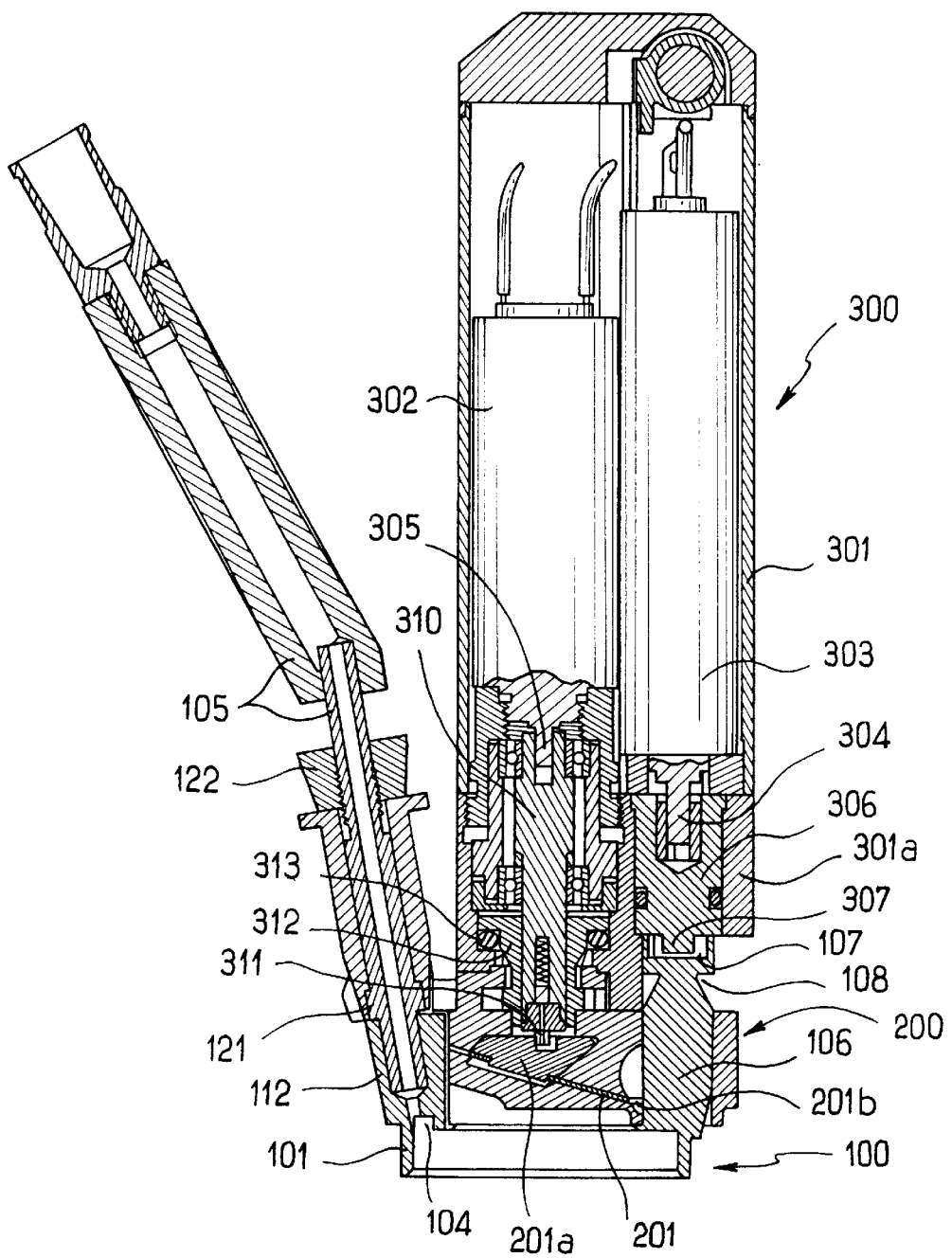
FIG_1

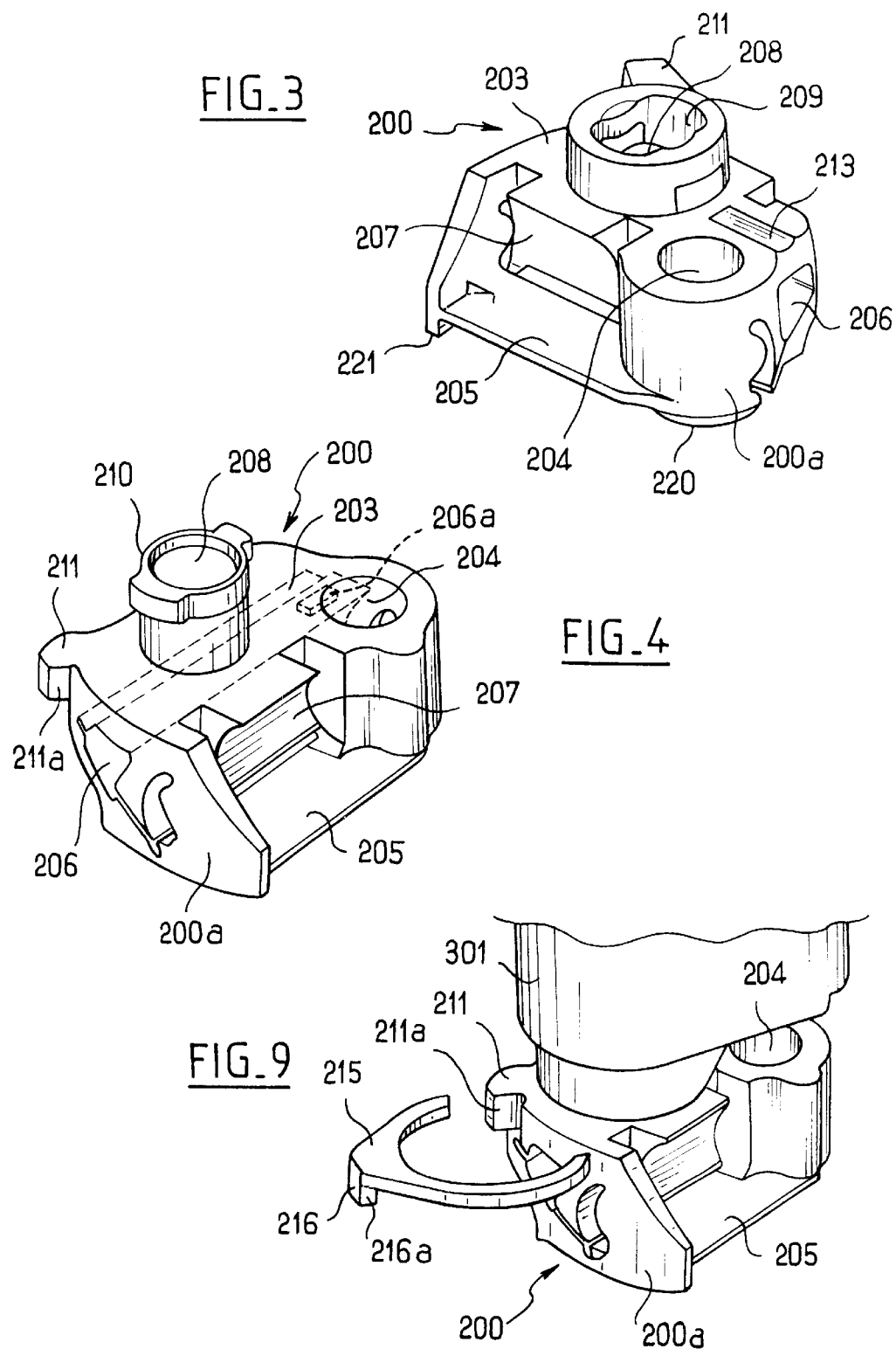

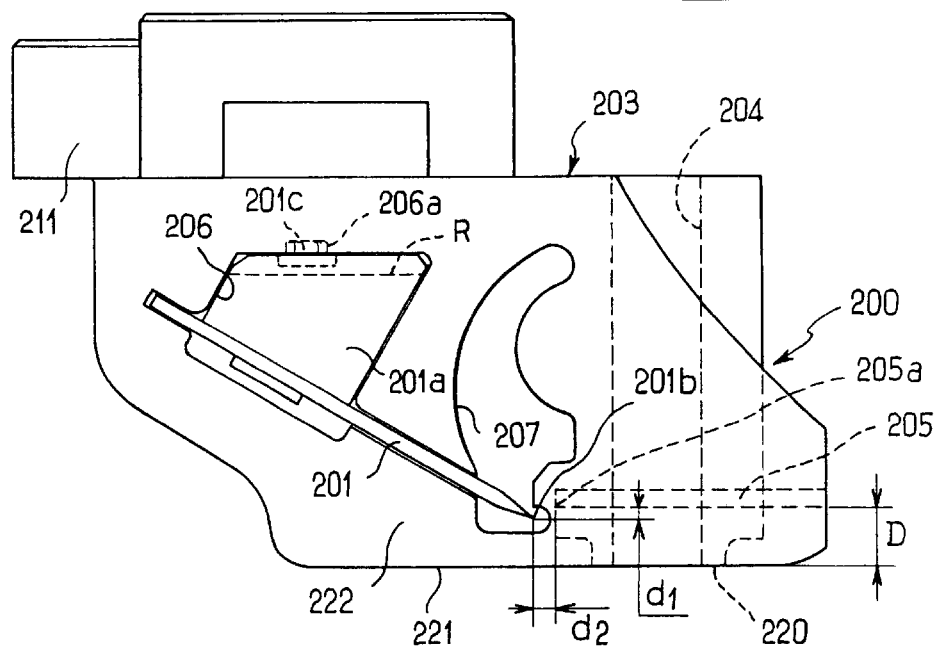
FIG.3A
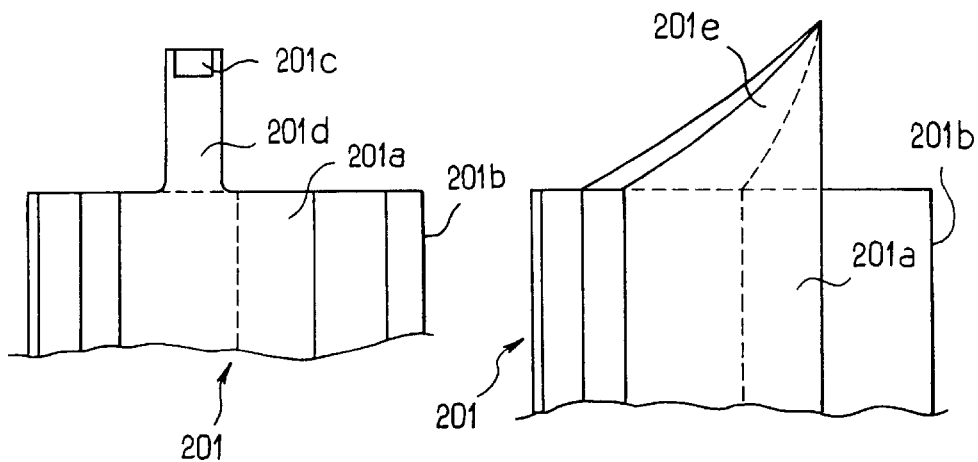
FIG.3B
FIG.3C

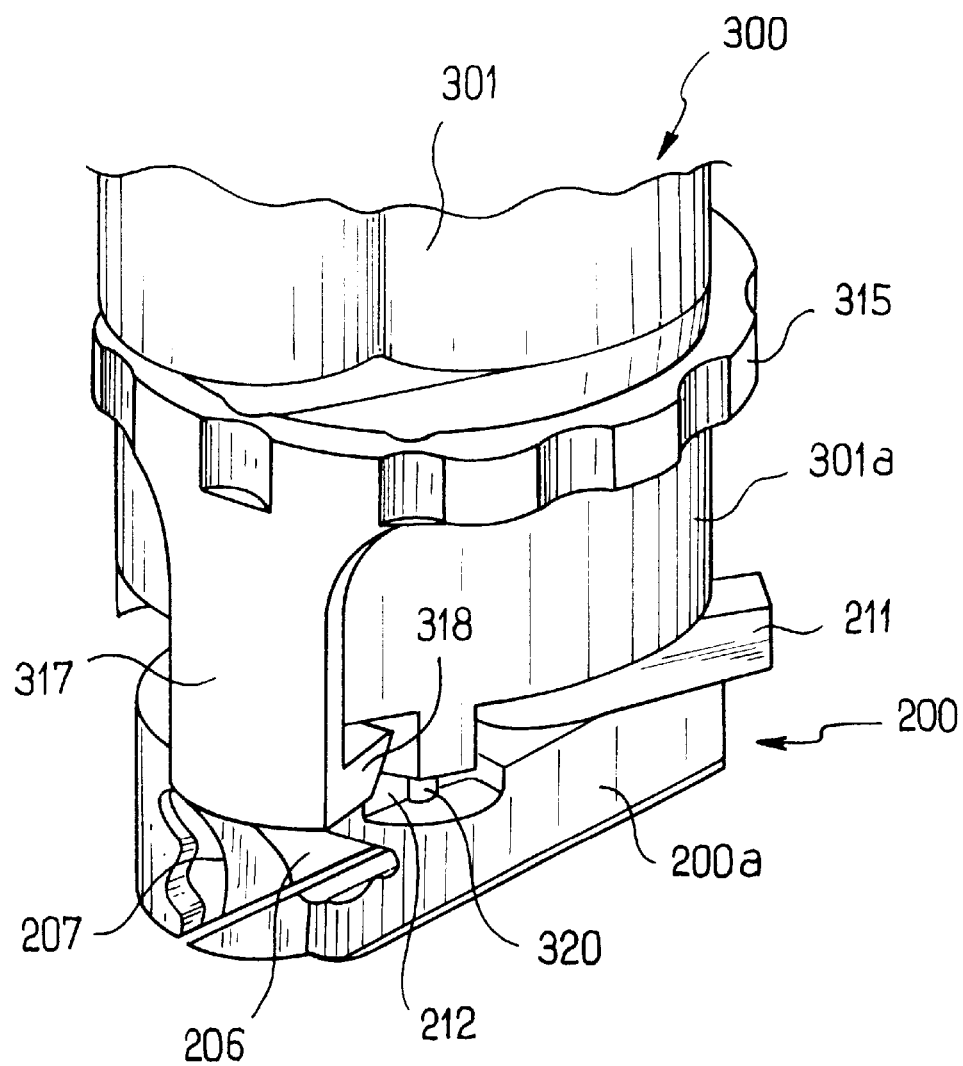
FIG_5

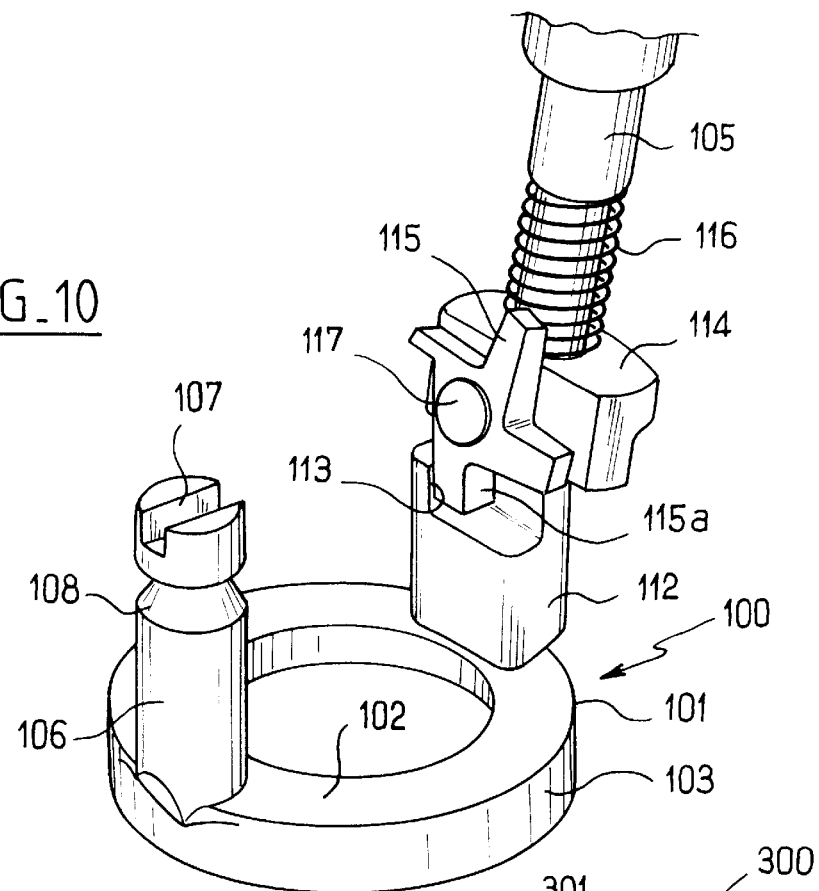
FIG_10
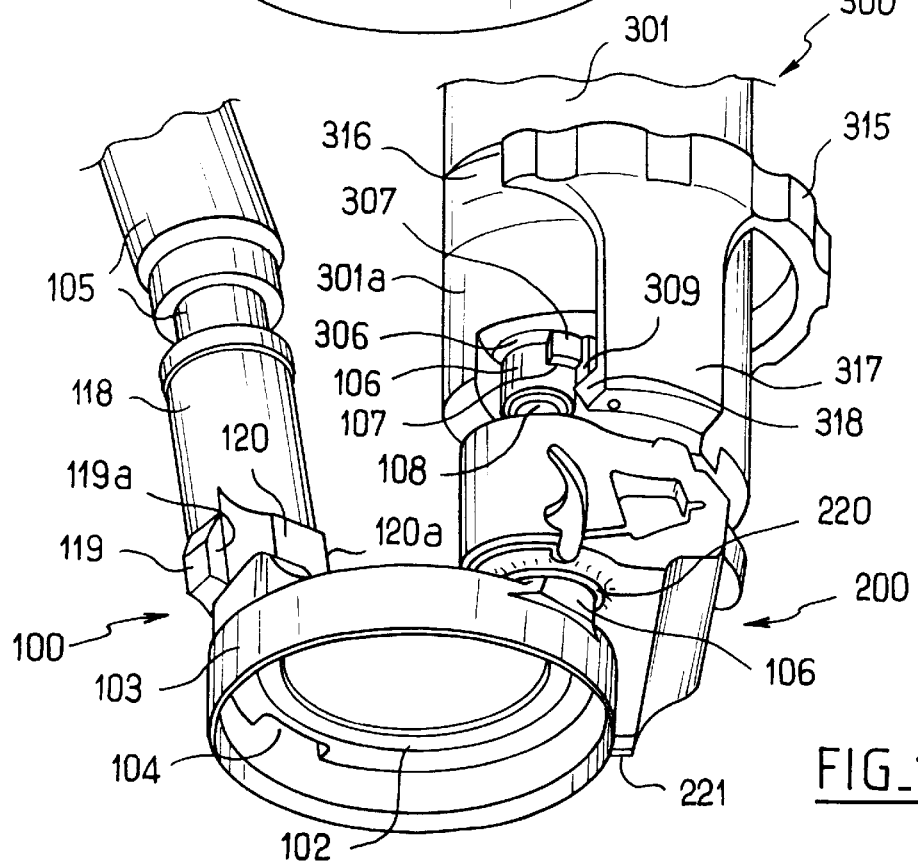
FIG_11

DEVICE FOR SURGERY OF THE CORNEA

The present invention relates to a device for surgery of the cornea, in particular a keratome capable of slicing a sliver from the cornea, either to separate it completely or to leave it as a flap.

BACKGROUND OF THE INVENTION

There exist numerous apparatuses suitable for implementing this operation (resection of the cornea). The technique of sliver resection began to be implemented more than 50 years ago and apparatuses have been under development ever since. This development has been directed essentially at two points: the means for cutting the corneal disk and the means for advancing the cornea-cutting means.

Two main types of cutter means are to be found at present: blades with circular motion (such as Prof. Draeger's microkeratome, for example) and blades with alternating rectilinear motion, including those which lie in the section plane (WO 95/31143) and those, in more widespread use, which slope relative to said plane like the blade of a planing tool (e.g. U.S. Pat. No. 4,462,370).

The blade is driven in the same way, i.e. by means of a motor or turbine whose rotary outlet shaft is connected to the blade either without any modification to its motion, in which case the blade is rotary, or else with the continuous circular motion of the motor being transformed into reciprocating linear motion by a peg secured to the shaft engaging in a groove secured to the blade which then oscillates in a direction perpendicular to the direction of its advance.

The means for moving the cutter blade through the cornea to be resected have in common a ring for fixing a base of the apparatus on the eye, which ring carries guide means that co-operate with a blade-carrier head within which the motion of the blade is sustained. These guide means are of two types, either slideways (generally rectilinear slideways) in which the blade-carrier head is slidably mounted (see document U.S. Pat. No. 4,662,370), or else a pivot about which the blade-carrier head is pivotally mounted (see document U.S. Pat. No. 5,586,980).

The movement of the blade-carrier head along the fixed guide means is driven by the hand of the surgeon. It is limited by an abutment when cutting of the cornea is to be limited to forming a flap that remains connected to the cornea. Proposals have recently been made to motorize this movement by causing rotating means carried by the blade-carrier head to co-operate with fixed means carried by the fixing ring so that the rotating means can roll without sliding along the fixed means (in this context, see the following documents: U.S. Pat. No. Re 35 421, U.S. Pat. Nos. 5,624,456, 5,980,543).

Present devices with motorized advance are devices which the surgeon finds complicated to use. It is not easy to adjust the beginning and the end of the cutting trajectory of the head, and there is no way to act on the travel speed of the blade-carrier head since there is only one motor for driving both the reciprocating motion of the blade and the gearing for advancing the keratome relative to the ring with a speed reduction that locks the frequency of oscillation of the blade and its speed of advance in a ratio that is defined by construction. Finally, those keratomes are not suitable for use by surgeons who prefer to apply manual control over the advance of the keratome across the ring.

OBJECTS AND SUMMARY OF THE INVENTION

The present invention seeks to remedy those drawbacks with a microkeratome that is simple to use and that offers the advantage of satisfying all of the requirements that have been expressed by surgeons.

To this end, the invention thus provides a device for surgery of the cornea, comprising:
- an annular base for fixing the apparatus to the eye of a patient;
- a cutter head comprising a body and a blade suitable for being displaced along a plane trajectory parallel to the annular base;
- guide means for guiding the cutter head relative to the base;
- drive means for driving the blade in the cutter head with reciprocating linear motion parallel to its cutting edge; and
- drive means for driving the cutter head relative to the annular base along said trajectory.

According to the invention, said drive means comprise two independent motor units surmounting the cutter head and having mutually parallel outlet shafts perpendicular to the plane of the trajectory of the cutter head.

The independence of these drive means provides numerous advantages. It is thus easy with simple electronic means for the operation of each of said means to be servo-controlled to determine fixed or variable parameters and to conditions defining a relationship between them.

Thus, the surgeon can adjust the rate of advance of the cutter head along its trajectory that makes it possible to adjust the rate of advance to the surgeon's own practices. The controlling electronics can provide for the cutter head to advance at a rate that varies, e.g. as a function of the variation in the surface area of cornea that is in contact with the blade. It is also possible to provide for oscillation to be interrupted during the return stroke of the cutter head.

It is also possible to provide safety features governing the drive which advances the head, specifically stopping the advance if oscillation stops or is faulty, making it impossible to start in the event of a failure of the suction system for holding down the annular base, . . . .

The two drives provided by the invention make it possible for the surgeon to fix the starting point of the trajectory accurately and without possible error so that, at the starting point, the blade is always out of contact with the cornea regardless of the diameter of the corneal cap that it is desired to obtain.

Finally, it should be observed that the independence of the drive means makes it possible to eliminate all of the mechanical gearing, wheel, and wormscrew means that used to be necessary and received in the head for taking transmission from the oscillation shaft for the purpose of advancing the cutter head. Unfortunately, such drive takeoff can only be performed via metal parts since they are the only parts that make it possible to achieve the manufacturing precision required for such small-sized equipment constituting micromechanics. The drive takeoff thus used to provide electrical continuity between the microkeratome motor and the fixing base or ring so the patient was not protected against electrical failure of the equipment during an operation. By eliminating this drive takeoff, the invention makes it possible to use a shaft of dielectric material (plastics material) at the outlet of the motor that drives advance of the head, thereby forming an insulating barrier between the electrical power supply of the motor and the fixing ring (base) in contact with the patient's eye.

BRIEF DESCRIPTION OF THE DRAWINGS

Other characteristics and advantages of the invention will appear on reading the following description of embodiments given below without limiting character.

Reference is made to the accompanying drawings, in which:

FIG. 1 is a longitudinal section view of a microkeratome of the invention;

FIG. 3 is an outside view of an embodiment of the body of the cutter head suitable for fitting to the end of the case as shown in FIG. 2;

FIG. 3A is a side view of a cutter head of the kind shown in FIG. 3 and fitted with a cutter blade;

FIGS. 3B and 3C are fragmentary plan views of blades suitable for use in a microkeratome of the invention;

FIG. 4 is an outside view of a variant embodiment of the body shown in FIG. 3;

FIG. 5 is an outside view of part of the case and of the cutter head assembled together with a device for locking the assembly on the annular base (not shown) for fixing the apparatus on the patient's eye;

FIG. 9 shows the cutter head coupled to its drive means, together with a member for adjusting the end point of the cutting stroke;

FIG. 10 is an outside view of the annular fixing base of the device, together with means for adjusting the end point of the stroke of the cutter head; and FIG. 11 is a view from beneath and in perspective of the device of the invention in which the annular base is a variant embodiment of that shown in FIG. 10, and the cutter head coupled to its drive means is as shown in FIG. 5.

MORE DETAILED DESCRIPTION

Figure 8:
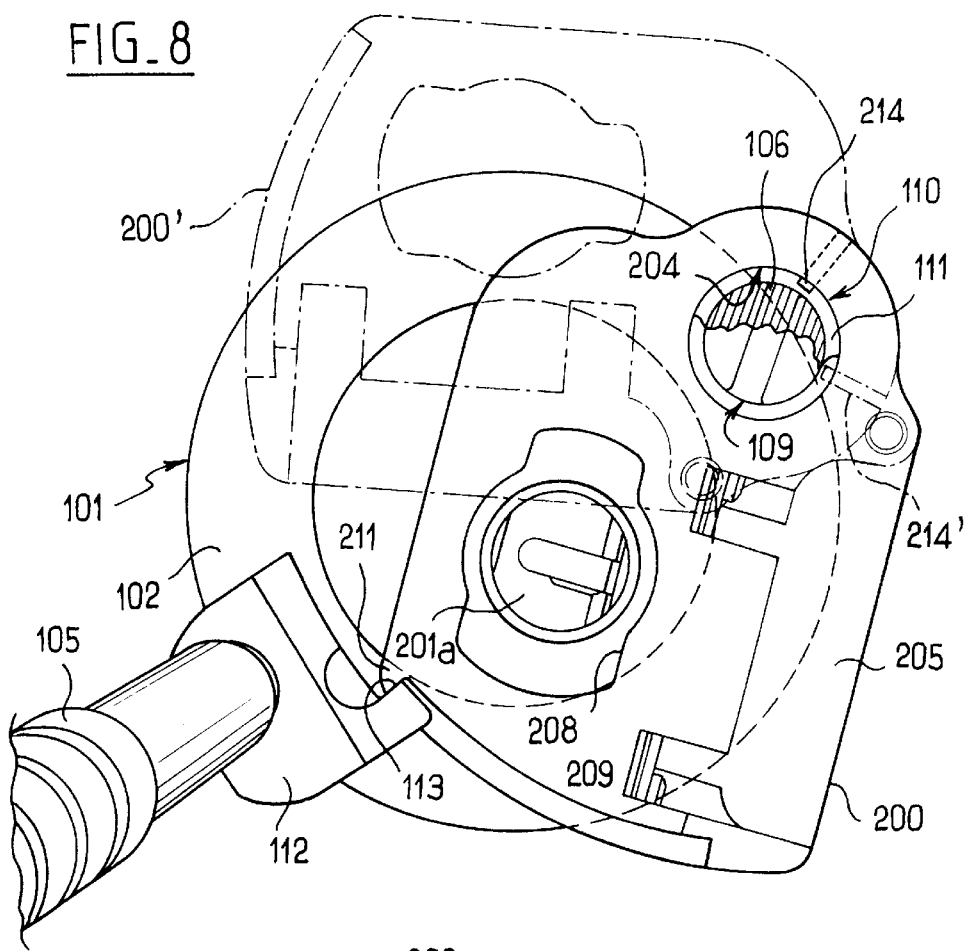
FIG. 8 is a simplified plan view of the device of the invention showing two extreme points of the trajectory of the cutter head relative to the annular base of the device.

The device for surgery of the cornea as shown in the drawings essentially comprises three portions. The first portion, given overall reference 100 in the figures, forms an annular base for fixing the device to the eye of a patient. The second portion, given overall reference 200 in the figures, constitutes a cutter head for using a blade 201 that it includes to cut off a disk of the cornea or to cut the cornea so as to leave a flap. The third portion 300 of the apparatus of the invention is constituted by drive means firstly for driving the cutter head 200 and secondly for driving the cutter blade 201 inside the cutter head.

The annular base 100, shown in particular in FIGS. 1, 8, 10, and 11 comprises a ring 101 formed by a flat annulus 102 fitted with a peripheral skirt 103. In conventional manner, the inner periphery of the flat annulus 102 and the bottom edge of the skirt 103 come into airtight contact with the eye of the patient and cooperate with the eye to define an internal annular chamber which is connected to a source of suction via an orifice 104 and a tube disposed inside a handle 105. Thus, the cornea to be operated on projects into the inside of the ring 101.

The ring possesses, integrally formed therewith, a pivot 106 which extends perpendicularly to the plane of the flat annulus 102. The top end of the pivot 106 is provided with portions in relief implemented in this case in the form of a mortise 107. In FIGS. 1, 10, and 11, this top end possesses, beneath the mortise 107, a groove 108. In FIG. 8, the pivot shown has at its top end a lateral surface with a first zone 109 of diameter smaller than a second zone 110, the zone 110 being fitted with a groove 111 whose bottom has the same diameter as the zone 109.

The pivot 106 is situated in a zone of the ring 101 that is substantially diametrically opposite the handle 105. The handle 105 is connected to the ring 101 via a bottom piece 112 which provides a substantially radial abutment surface 113. In the case shown in FIG. 10, the handle 105 has a sliding piece 114 fitted with a set of spacers 115 formed on a star-shaped piece whose branches are of different thicknesses. The piece 114 is pressed against the piece 112 by means of a spring 116. It will be understood that when the piece 114 is raised against the spring 116 along the handle 105, the branches of the star-piece 115 are disengaged from the abutment 113, thus making it possible to select the branch of appropriate thickness for coming into abutment against the surface 113. Each of the branches then offers a surface 115a in front of the surface 113 and spaced apart therefrom by a distance equal to the thickness of the branch. It will be observed that the piece 115 is mounted to rotate about a pin 117 carried by the piece 114.

In the case shown in FIG. 11 and in FIG. 1, the handle 105 possesses an outer sleeve 118 fitted at its bottom end with a plurality, e.g. three protuberances 119, 120. This sleeve can be indexed angularly about the handle 105 so that one of the protuberances 119, 120 presents an abutment surface 119a or 120a similar to the abutment surface 113 or the abutment surface 115a of FIG. 10. The protuberances 119 and 120 are of different circumferential sizes so that the abutment-forming surfaces 119a and 120a are angularly closer to or further from the pivot 106 depending on the size of the protuberance. The sleeve 118 can be indexed about the handle 105 by means of a fluted portion 121 of the handle covered by a correspondingly fluted portion of the sleeve 118, a nut 122 in screw engagement on the handle 105 enabling the sleeve 118 to be pressed against the handle-receiving piece 112 while it is engaged with the fluting 121, or when the nut is loosened, enabling the sleeve 118 to be slid so as to change the protuberance that is in service. It would not go beyond the ambit of the invention to provide a spring at the top of the sleeve 118 instead of and replacing the nut 122, like the spring shown in FIG. 10.

The cutter head 200 visible in FIGS. 1, 3, 3A, 4, 5, 8, 9, and 11 is of a general shape that is already described in the art. This cutter head possesses a one-piece body 200a having a top surface 203. It has a bottom surface which is its surface that faces towards the fixing ring 101 to slide thereon. In the example shown in the figures, it comprises no more than a surface 220 and a surface 221, both lying in a common plane. The body possesses firstly a through orifice 204 opening out into the surfaces 220 and 203 and suitable for receiving the pivot 106. This body also defines, perpendicularly to the axis of the orifice 204, a shelf 205 whose bottom face is spaced apart from the surfaces 220 and 221 and whose function is to flatten the cornea immediately ahead of the cutter blade. The body 200a also possesses, following the shelf, an orifice 206 for receiving and guiding the cutter blade 201 shown in FIGS. 1, 3A, 3B, and 3C. This cutter blade 201 possesses a support 201a with a groove R formed in the top surface thereof perpendicularly to the cutting edge 201b of the blade, which cutting edge is substantially parallel to the rear edge of the shelf 205, the groove being for receiving an eccentric finger on the outlet shaft of the blade drive motor. The housing 206 opens out immediately behind the shelf 205 so as to enable the blade to project and its cutting edge 201b to be situated beneath the bottom face of the shelf 205 and behind its rear edge 205a by a calibrated distance (d1, d2) which depends on the thickness of the corneal flap to be made. The body 200a presents a deflector surface 207 above said opening and immediately behind the shelf 205, where such a surface 207 is likewise well known in the state of the art and forms a sliding surface over which the corneal flap slides as cutting progresses.

An orifice 208 parallel to the orifice 204 opens out into the inside of the housing 206 from the top surface 203 of the body. In FIG. 3, it can be seen that the orifice 208 is extended by means 209 of the female bayonet coupling type which enable the head to be coupled to the end of the keratome drive means 300. In FIG. 4, the bayonet means are represented as being in the form of a sleeve 210 with studs that penetrate into and co-operate with female means provided in the drive means 300. The orifice 208 enables the blade drive finger to reach the groove R in the blade support 201a.

It will be observed that the body 200a has a lateral projection 211 in the vicinity of its top surface 203, which lateral projection has a surface 211a substantially parallel to the axis of the orifice 204, said surface forming abutment means for co-operating with one of the surfaces 113, 115a, 119a, or 120a provided on the angular base of the device.

The housing 206 for the blade 201 and its blade-carrier 201a can either pass right through the body 200a of the cutter head 200, or else can be limited by an end partition. The partition could be a web in continuity with the side surface of the head shown in FIG. 3 adjacent to the bore 204.

With a through orifice, as is provided mainly in a multiple-use head made of metal, it is necessary to prevent the assembly comprising the blade 201 and the blade-carrier 201a from escaping from its housing once it has been inserted therein, before the head is mounted on the motor assembly 300, and while the surgeon is performing the manipulations necessary to achieve said mounting. For this purpose, the housing 206 possesses a small cavity 206a for receiving a stud 201c carried at the end of a resilient tongue 201d which is integral with the support 201a of the blade 201 (see FIGS. 3A, 3B, and 4). While the blade is being inserted into the cavity 206, the tongue 201d is curved elastically until the stud 201c rises and is received in the housing 206. The blade is then retained in the housing 206. It can nevertheless oscillate in said housing 206 under drive from the eccentric drive finger since the length of the cavity 206a measured in the oscillation direction is greater than the amplitude of said oscillation. The blade is also held in the housing in a position such that the groove R of the support is held in a region of the head which is necessarily scanned by the eccentric drive finger as soon as the motor begins to rotate, and possibly as soon as the head is mounted on the drive block 300. In this respect, it is advantageous for the groove R to flare upwards so that penetration of the drive finger is facilitated.

When the housing 206 is closed by an end web, as is the case mainly for a single-use head 200 made of plastics material, it needs to be delivered fitted with its blade. The stud 201c then serves as a member for holding the blade in the single-use head 200 from manufacture until use.

In a variant embodiment of the blade 201, shown in FIG. 3C, the support 201a is provided with a projecting tip 201e extending beyond the edge of the blade 201 and which serves as a guide for inserting the blade in the housing 206.

When the cutter head 200 is mounted to pivot about the pivot 106, its trajectory is plane, perpendicular to the axis of the pivot 106, and thus parallel to the ring 101.

The drive means 300 comprise a case 301 containing two motor units 302 and 303, whose bodies are prevented from rotating relative to the case, and which have respective outlet shafts 304 and 305. The outlet shaft 304 of the motor unit 303 has an extension shaft 306 secured thereto and constrained to rotate therewith, with the end 307 of the extension shaft 306 being close to the end 301a of the case. The end 307 of this extension shaft 307 is in the form of a tenon of dimensions that adapt it for penetrating without clearance into the mortise 17 situated at the top of the pivot 106.

Figure 2:
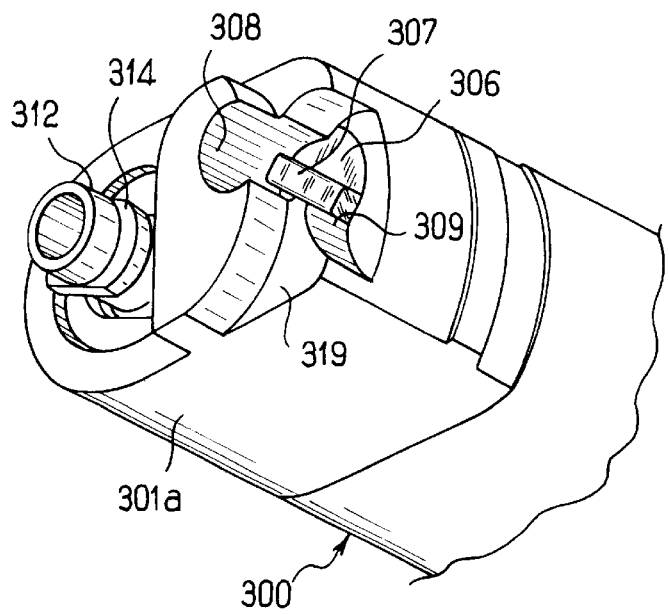
FIG. 2 is an outside view of the end of the common case for the two motors whereby said case is coupled to the cutter head.

In FIG. 2, it will be observed that the end 301a of the case 301 is a machined part of relatively complex shape, having, in line with the shaft 306, a partially cylindrical recess 308 on the same axis as the shaft 306 but of smaller diameter, such that one of the edges 309 of this recess forms an angular abutment for the tenon 307. The tenon 307 does not have the same length as the diameter of the shaft 306, but it is shorter so that one of its ends can rotate freely in the recess 308 while its other end is constrained to come into abutment against the edge 309 thereof. It will be understood that this edge 309 thus constitutes an abutment for angularly indexing the tenon 307 relative to the case 301.

The outlet shaft 305 of the motor 302 is also extended by a shaft 310 whose end has an eccentric finger 311 for driving the blade 201. This shaft 310 is surrounded at its end with a sleeve 312 (only the sleeve 312 is shown in FIG. 2, the shaft 310 being omitted in order to clarify the drawing), said sleeve 312 being constrained in rotation relative to the end piece 301a of the case 301, but being capable of a small amount of axial displacement along the shaft 310 against an annular rubber spring 313 which tends to cause it to retract somewhat into the end piece 301a. The sleeve 312 is provided with a collar 314 of non-circular shape that provides male bayonet coupling means for engaging the female bayonet coupling means 209 of the body 200a of the cutter head 200, as shown in FIG. 3.

Figure 6:
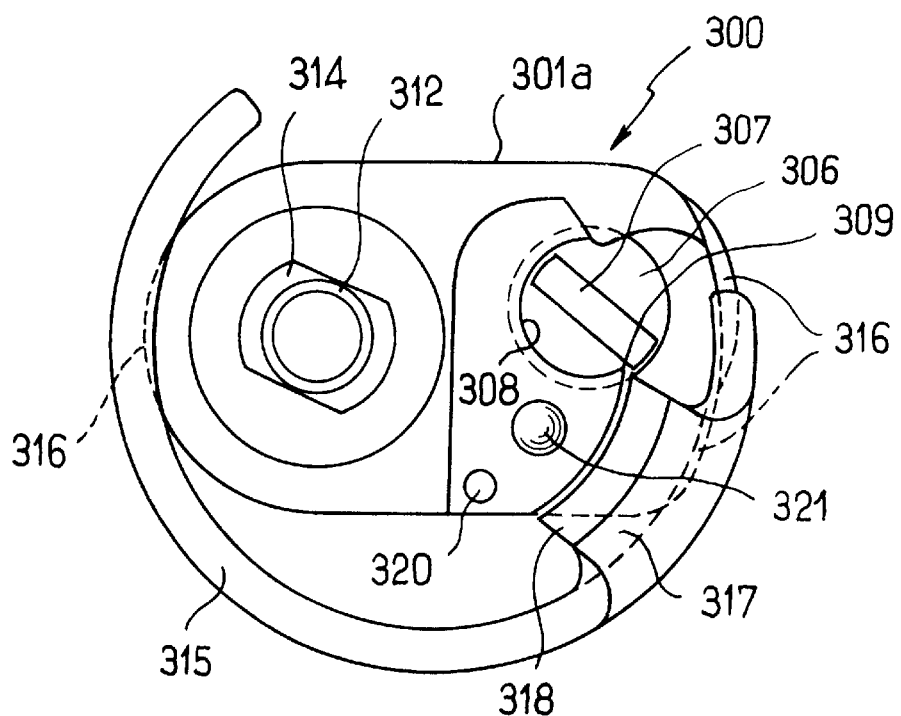
FIG. 6 and FIG. 7 are two views of the underside of FIG. 5 showing the inactive and the active states of the locking device.
Figure 7:
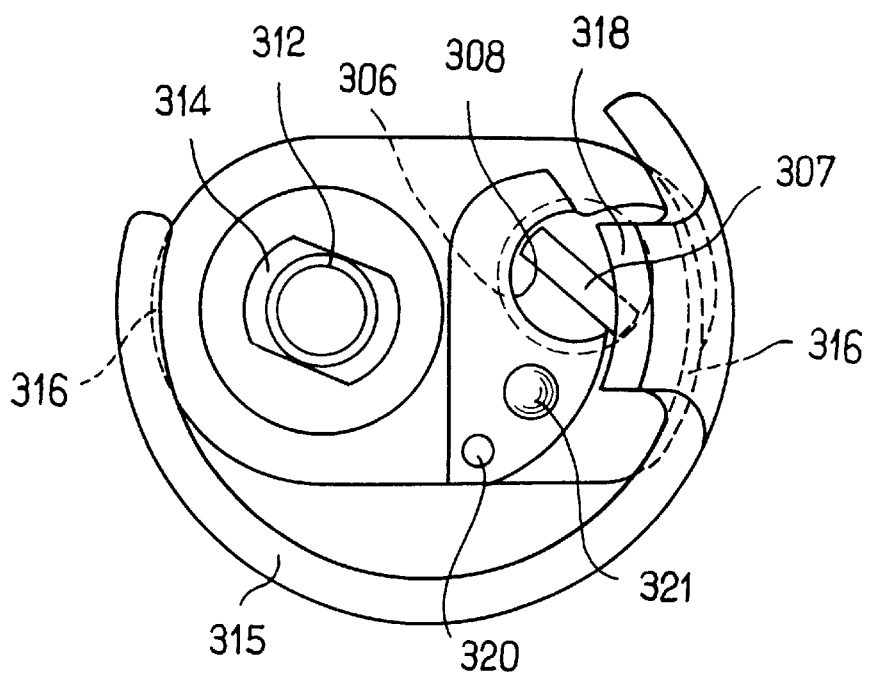

FIGS. 5, 6, and 7 show the elements 300 and 301a fitted with a latch formed by a ring portion 315 mounted to rotate in a groove 316 of the piece 301a. This ring 315 has a downwardly extending arm 317 provided with an inwardly directed tooth 318, said tooth extending at a level that is slightly offset from the tenon 307 towards the free end of the piece 301a. As can be seen in FIGS. 6 and 7, when the ring 315 is in an inactive state (FIG. 6), the tooth 318 is received in a recess 319 of the end piece 301a. When it is in an in-service state (FIG. 7), the tooth 318 interferes with the recess 308 so that when the pivot is received in said recess it penetrates into the groove 108 of the pivot and prevents any axial separation between the annular base 100 and the piece 301a, which naturally carries the cutter head 200.

In order to perform an operation, the surgeon begins by assembling the cutter head 200 already fitted with its cutter blade 201 to the drive means 300. To do this, the means 209 of the head 200 are engaged with the means 314 at the end 301a of the assembly 300. The fixed angular orientation of the means 314 is such that this engagement can be achieved only if the head is offset angularly relative to the piece 301a, i.e. if the axes of the housing 204 and of the shaft 306 do not coincide. Once axial engagement has been achieved, the surgeon pivots the head 200 about the axis of the shaft 310 received inside the means 314 SO that they co-operate like a bayonet coupling with the means 209, thus preventing any axial separation of the head 200 from the case 301. This rotation is done so as to move the axis of the orifice 204 towards the axis of the shaft 306. These axes are brought into alignment when, for example, an abutment 320 (a peg) comes to bear against a surface 212 of the body 201 of the cutter head (see FIG. 5). Advantageously, provision is also made for the head to be indexed on the case, e.g. by means of a flute 213 (FIG. 3) formed in the top surface 203 of the head which receives a ball 321 (FIG. 6 and FIG. 7) projecting under drive from a return spring from the end face of the piece 301a.

It will be understood that the head 200 of FIG. 4 is mounted on the body of the case 301 in the same manner except that the male and female bayonet coupling means are interchanged compared with the above example. In this respect, it will be observed that the means 210 which perform this bayonet coupling are not symmetrical, thus constituting keying means to ensure that the head cannot be wrongly mounted to the motor assembly case. Such asymmetrical coupling means can also be used in the preceding embodiment.

Once the elements 200 and 300 have been assembled together in this way and prevented from moving axially and angularly relative to each other, the orifice 204 of the head 200 is in alignment with the shaft 306. It will be observed that the shaft 306 possesses control means such that after an operation has been performed it is returned to a fixed angular position which is the position shown in FIG. 2, i.e. the tenon 307 bears against the surface 309 of the piece 301a. The surgeon places the annular base 100 on the patient's eye and holds it there by suction as described above. Thereafter, the assembled-together elements 200 and 300 are presented thereto so as to insert the pivot 106 in the orifice 204. To ensure that the tenon 307 penetrates into the mortise 107, the surgeon must cause the set of elements 200 & 300 to pivot about the pivot 106, thereby defining one and only one relative angular position between the base 100 and the assembled elements 200 & 300. This position is the starting position for the operation. It is reached when the cutter blade is spaced apart from the cornea that is to be operated on specifically because the tip of the tenon 307 rests against the tip of the pivot 106 until the tenon penetrates into the mortise. This provides additional safety preventing any unwanted injury to the cornea by the cutter blade. When the tenon 307 has penetrated into the mortise 107 the assembled motor 300 and cutter head 200 rest against the annular base 100 via the two coplanar surfaces 220 (surrounding the orifice 204) and 221 (at the end of the lateral wall 222 of the body 200a of the cutter head 200 see FIGS. 3 and 3A). It will be understood that by varying the vertical distance D (FIG. 3A) between the bottom face of the shelf 205 and said surfaces 220, 221 it is possible to vary the extent to which the portion of the cornea projecting into the center of the annular base 100 is compressed by the shelf 205. Thus, the smaller this distance the greater the extent to which the cornea is flattened; this means that a corneal cap of larger diameter is obtained than with a larger value for D. Thus, other things remaining equal, by providing a set of cutter heads 200 each having a different value for the distance D, the surgeon can be given the possibility of choosing the diameter of the corneal cap that is to be obtained, so as to adapt said diameter in the best possible manner to the needs of the patient.

The trajectory followed by the cutter blade is thus circular, being centered on the axis of the pivot 106 and lying in a plane perpendicular to the axis of said pivot. By construction, the axes of the motors 302 and 303 are then parallel to the axis of the pivot 106 and thus perpendicular to the trajectory followed by the cutter blade. It will be observed that this ensures there is practically no overhang of the moving assembly relative to the fixed annular base throughout the entire procedure for cutting the cornea. The weight of the motor 303 acts practically along the axis of the pivot, and the weight of the motor 302 acts along an axis which never projects beyond the peripheral skirt 103 of the annular base. The resultant of these two gravity forces therefore always lies inside the annular base.

To implement an axial security link between the annular base and the moving assembly 200, 300, the invention provides various devices.

Firstly, there is the latch shown in FIGS. 5, 6, 7, and 11. When it is in the state shown in FIGS. 6 and 11, the latch does not interfere with the pivot head which has passed through the orifice 204 and which is engaged with the tenon 307. By turning the ring 315 so as to bring the latch into its active state, the tooth 318 is caused to pass under the pivot head 106 so as to be received in the groove 108 of the pivot. It is then impossible to separate the moving assembly 200, 300 from the ring 100, or for this moving assembly to be accidentally lifted during an operation. The figures do not show the indexing and abutment devices which are provided between the ring 315 and the piece 301a to enable the surgeon to feel the two positions of the latch and to ensure that the latch is not forced in a direction that would be harmful to the mechanical quality of the equipment. These devices can merely be resilient snap-fastening systems and pegs that come into abutment against suitable surfaces.

This locking function can be performed differently, as shown diagrammatically in FIG. 8. In this figure, continuous lines show the head 200 at the end of its working stroke, and chain-dotted lines show the head 200' at the moment when the tenon 307 penetrates into the mortise 107. The body of the head 200a carries a stud 214 which projects into the orifice 204 in a well-determined angular position. When the tenon 307 penetrates into the mortise 107, the stud 214 is situated facing the lateral zone 109 of the pivot 106 which is of diameter smaller than the inside diameter of the orifice 204, thus enabling the projecting portion of the stud 214 to avoid interfering with axial sliding of the head over the pivot 106. This stud is then in its position 214', i.e. immediately at the entrance to the groove 111 which carries the zone 110 of the pivot which is itself of a diameter substantially equal to the inside diameter of the orifice 204. It will be understood that as soon as pivoting of the head 200 about the pivot 106 is initiated in order to move it from its position 200' to its continuous line position in FIG. 8, the stud 214 engages in the groove 111. Throughout the duration of cutting and return of the moving portion about the pivot 106, no axial separation is possible between the moving portion 200 & 300 and the fixed annular base. With a microkeratome that is suitable for being fitted with a selection of heads that differ from one another as to the value D shown in FIG. 3A, then the invention provides axial security link means that accommodate these different sizes in simple manner.

In a first variant (not shown), the annular base 100 possesses a removable pivot 106 (e.g. because it is secured to the ring by screw engagement), thus enabling the pivot to be matched with the head used. For a head with a small value of D, the tenon 307 and the tooth 318 of the ring 315 are closer to the top surface of the ring 101. The corresponding pivot for fitting to the ring should therefore be shorter than for a head with a larger value of D so that the tenon 307 does not come into abutment against the bottom of the mortise 107 and the groove 108 is not too high relative to the tooth 318.

In another variant, a single base 100 can be provided for all of the heads by making a mortise 107 that is sufficiently deep to receive a tenon 307 that is sufficiently long to accommodate all differences in height between the cutter heads because of the different dimensions D. To adjust the link mechanism, an arm 317 is then provided that is of a length which is adjustable by means of two telescopic portions and an indexing system for causing the length of the arm to correspond to the selected head.

In a third variant, the keratome of the invention has a set of heads 200 with each having a distance D that is determined as a function of the diameter of the corneal cap to be obtained, and a complete set of angular bases each corresponding to one of the heads. These dispositions are advantageous, particularly when single-use cutter heads and bases are provided that are made out of synthetic material.

As described above, the starting point of the trajectory followed by the cutter head is determined by the angular orientation of tenons in the piece 301a. The surgeon can then switch on the motor 302 which gives rise to high frequency reciprocating motion of the blade 201. The surgeon then switches on the motor 303. Since the shaft 306 associated with this motor cannot turn because of the tenon-mortise connection between said shaft 306 and the fixed pivot 106, it is the body of the motor that turns about the shaft 306, and thus the entire case 301 and the cutter head 200 which is associated therewith. This moving assembly stops turning when the lateral projection 211 secured to the cutter head 200 comes into abutment against one of the surfaces 113, 115a, 119a, or 120a depending on the embodiment shown, which surfaces are all carried by a piece that is secured to the annular base 100. By means of a suitable detector, e.g. responsive to an increase in the power supply current drawn by the motor 303, the power supply to the motor is switched off or reversed so as to cause the head to return to its initial position. It is recalled that this initial position is obtained by the tenon 307 coming into abutment against a surface 309 carried by the piece 301a. In this case, likewise by means of an appropriate sensor, the sudden increase in torque opposing rotation is detected and the power supply to the motor 303 is switched off. The portions 200 and 300 can then be removed from the annular base 101 and any desired intrastroma ablation can be performed while keeping the corneal cap raised, in particular by using a procedure known under the name LASIK.

It will be understood that the final position of the cutter head determines the position, the length, and thus the mechanical qualities of the "hinge" link zone between the flap that has just been cut free and the eye. The surgeon must be capable of acting in this final position. It must thus be possible to move the abutment surface 113 that is secured to the annular base 100. For this purpose, the invention proposes a variety of embodiments to achieve this result, as shown respectively in FIGS. 10, 11, and 9.

By using the device described above with reference to FIG. 10, the surgeon can replace the abutment surface 113 with a selected one of four available surfaces 115a thus enabling the position of the end point of the trajectory of the cutter head to be adjusted.

In FIG. 11, it is the surfaces 119a and 120a that can be put selectively into operation by rotating the sleeve 118 carrying them so as to achieve the same result.

Finally, FIG. 9 proposes a third variant embodiment in which action is no longer taken on the surface 113 secured to the annular base 100 but on the surface 211a secured to the projection 211 carried by the body 200a of the cutter head. When the head 200 is assembled to the case 301, the case has an outside surface suitable for receiving a kind of clip 215 which possesses a spacer 216 capable of bearing against the surface 211a of the projection 211 and thus of presenting an abutment surface 216a that co-operates with the surface 113 of the piece 112 of the base 100. The surgeon has a set of clips 215 so as to have spacers 216 of a sufficient variety of different thicknesses to be able to obtain the desired adjustment.

The above description relates to an embodiment of the main means of the invention applied to a pivoting keratome. It would not go beyond the ambit of the spirit of the invention to provide two motors for a keratome having linear motion or even pivoting motion obtained by co-operation between gears provided outside the head 200 and fixed racks provided on the annular base. Although the motor for driving the blade in its reciprocating motion inside the cutter head remains substantially identical in all variant embodiments, the motor 303 can have its outlet shaft 306 engage a transmission, e.g. using gear wheels, with the last gear wheel meshing with a fixed rack that can be rectilinear or curved.

It will be observed that having independent motors provides numerous advantages to the surgeon as to flexibility in use of the microkeratome. In addition to those mentioned above, it can also be mentioned that the surgeon finds it reassuring to be able to start the oscillating motion of the blade before starting the cutting movement of the cutter head, and it can be advantageous to continue the oscillating motion of the blade even after the movement of the cutter head has stopped.

Another advantage of two motors lies in enabling two types of microkeratome to be manufactured on a standardized basis, one type having motor-driven advance and the other manual advance. For a manual advance keratome, the only modification that needs to be made to the keratome described above is minor and lies in omitting the mortise 107 at the end of the pivot 106. Under such circumstances, the surgeon can actuate the assembled elements 200 and 300 manually about the pivot 106 after locking them to the pivot. Nevertheless, this loses the advantage of having a starting position that is determined and fixed. To retain this advantage, a simple modification to the keratome of the invention consists in omitting the motor 303 and in replacing it with a piece that has an end tenon like the shaft 306. This piece is subject to a relatively small amount of return torque about its longitudinal axis thus pressing the tenon against the surface 309 of the piece 301a as described above. Under such circumstances, the three portions of the keratome are assembled together and mounted in the same manner as that described above, with the manual advance movement of the cutter head over the ring of the annular base being performed manually against the member which exerts the above-mentioned return torque on the tenon. Finally, this manual version is easy to motorize. All that is needed is to perform the opposite substitution to that described above, i.e. the peg having a tenon with return torque applied thereto is replaced by a motor unit such as the unit 303 as described above.

We claim:

1. A device for surgery of the cornea, the device comprising:
    an annular base for fixing the apparatus to the eye of a patient;
    a cutter head comprising a body and a blade having a cutting edge suitable for being displaced along a plane trajectory parallel to the annular base;
    guide means for guiding the cutter head relative to the base;
    drive means for driving the blade in the cutter head with a reciprocating linear motion parallel to the cutting edge; and drive means for driving the cutter head relative to the annular base along said trajectory;

wherein said drive means comprise two independent motor units surmounting the cutter head and having mutually parallel outlet shafts perpendicular to the plane of the trajectory of the cutter head.

2. A device according to claim 1, wherein the two motor units are received in a common case possessing an end surface from which there projects a drive shaft for driving the cutter blade, the case having coupling means for coupling with the cutter head.

3. A device according to claim 2, wherein the coupling means for coupling to the cutter head comprise bayonet means for connecting said head to the case so as to prevent the body of the head and the case from moving relative to each other along the axis of the drive shaft for driving the blade, and abutment means between the case and the body of the head to index the body and the case in a determined angular position about the axis of the drive shaft for driving the blade.

4. A device according to claim 3, wherein the bayonet coupling means comprise a sleeve surrounding the projecting portion of the drive shaft for driving the blade and a recess of complementary shape in the body of the cutter head.

5. A device according to claim 3, wherein the bayonet coupling means comprise a recess on the axis of the blade drive shaft formed in the end of the case and a sleeve projecting from the body of the cutter head, for co-operating on the outside with said recess and for receiving on the inside the blade drive shaft.

6. A device according to claim 2, wherein the drive motor unit for driving the cutter head relative to the annular base has a shaft whose end is situated in the vicinity of the end surface of the case and possess portions in relief arranged at the end of the shaft to co-operate by axial engagement with portions in relief arranged at the end of a fixed pivot carried by the annular base and parallel to the axes of the motor units.

7. A device according to claim 6, wherein the body of the cutter head possess a cylindrical recess passing right through its thickness and on the same axis as the shaft which is provided with end portions in relief when the body of the cutter head is angularly indexed relative to the case.

8. A device according to claim 7, including, between the pivot and the case or the body of the cutter head, means for axially connecting the pivot and the shaft having end portions in relief at least during the movement of the cutter head about the pivot.

9. A device according to claim 8, wherein the axial connection means include a member for controlling their activated and deactivated states, the member being in the form of a ring mounted to turn on the case about an axis parallel to the axes of the motors.

10. A device according to claim 6, wherein the shaft having end portions in relief and the case possess abutment means defining a determined angular position relative to the case for the shaft having end portions in relief.

11. A device according to claim 10, wherein the determined angular position between the shaft having end portions in relief and the case determines the starting position for the trajectory of the cutter head when making the rotary connection between the shaft and the pivot.

12. A device according to claim 6, wherein the annular base includes, in a zone that is substantially diametrically opposite the fixed pivot, an abutment for limiting the pivoting of the body of the cutter head relative to the base, for co-operating with a radial projection of said body of the cutter head.

13. A device according to claim 12, wherein the abutment and/or the radial projection are adjustable in position on the annular base and/or on the body of the cutter head.

14. A device according to claim 1, comprising a set of cutter heads in which each cutter head includes a flattening shelf spaced apart from a sliding surface of the head on the base by a distance D that is different from said distance for all of the other heads of the set.

15. A device according to claim 1, wherein the cutter head has a housing for guiding the cutter blade during said reciprocating linear motion, which housing possesses means for holding the blade inside the housing.

16. A device for surgery of the cornea, the device comprising:

a base having an aperture to receive an eye of a patient;

a cutter head including a body and a blade, said blade having a cutting edge, said cutter head being attached to said base and moveable along a path in a first plane, said path at least partially crossing said aperture of said base;

a guide attached to said base which engages said cutter head and guides said cutter head along said path in said first plane;

a first motor having a first output shaft causing a reciprocating motion of said blade; and a second motor, independent of said first motor, having a second output shaft causing said cutting head to move along said path, wherein at least one of said first and second output shafts extends perpendicular to said first plane.

17. A device according to claim 16, wherein both of said first and second output shafts extend perpendicular to said first plane.

18. A device according to claim 16, further comprising:

a common casing which houses said first and second motors, said common casing coupling to said cutter head.

19. A device according to claim 16, further comprising:

a user settable stop for selectively setting an end of said path of said cutter head.

20. A device according to claim 19, wherein said user settable stop includes a rotatable member having a plurality of abutment surface thereon, and wherein a user rotates said rotatable member to bring one of said plurality of abutment surfaces into a preset position in order to selectively set said end of said path of said cutter head.

* * * * *